(12) United States Patent
Elliott et al.

(10) Patent No.: US 9,883,905 B2
(45) Date of Patent: Feb. 6, 2018

(54) ELECTROSURGICAL PROBES FOR SUCTION AND IRRIGATION SYSTEMS

(71) Applicant: Applied Medical Resources Corporation, Rancho Santa Margarita, CA (US)

(72) Inventors: Patrick Elliott, Rancho Santa Margarita, CA (US); Daniel McFarland, Rancho Santa Margarita, CA (US); Michael Whitlock, Rancho Santa Margarita, CA (US); Wayne Young, Brewster, NY (US)

(73) Assignee: Applied Medical Rescources Corporation, Rancho Santa Margarita, CA (US)

( * ) Notice: Subject to any disclaimer, the term of this patent is extended or adjusted under 35 U.S.C. 154(b) by 699 days.

(21) Appl. No.: 14/505,105

(22) Filed: Oct. 2, 2014

(65) Prior Publication Data

US 2015/0094709 A1    Apr. 2, 2015

Related U.S. Application Data

(60) Provisional application No. 61/885,562, filed on Oct. 2, 2013.

(51) Int. Cl.
*A61B 18/14* (2006.01)
*A61M 1/00* (2006.01)
*A61B 17/00* (2006.01)
*A61B 18/00* (2006.01)

(52) U.S. Cl.
CPC .......... *A61B 18/14* (2013.01); *A61B 18/1482* (2013.01); *A61M 1/0064* (2013.01); *A61M 1/0084* (2013.01); *A61B 2017/00477* (2013.01); *A61B 2018/00035* (2013.01); *A61B 2018/00172* (2013.01); *A61B 2018/00178* (2013.01); *A61B 2018/00196* (2013.01); *A61B 2018/1422* (2013.01); *A61B 2218/002* (2013.01); *A61B 2218/007* (2013.01)

(58) Field of Classification Search
CPC .. A61B 18/14; A61B 18/1482; A61M 1/0064; A61M 1/0084
See application file for complete search history.

(56) References Cited

U.S. PATENT DOCUMENTS

| | | |
|---|---|---|
| 5,195,958 A | 3/1993 | Phillips |
| 5,322,503 A | 6/1994 | Desai |
| 5,322,506 A | 6/1994 | Kullas |
| 5,505,710 A | 4/1996 | Dorsey, III |
| 5,562,640 A | 10/1996 | McCabe et al. |
| 5,573,504 A | 11/1996 | Dorsey, III |
| 5,586,977 A | 12/1996 | Dorsey, III |
| 5,607,391 A | 3/1997 | Klinger et al. |
| 5,792,139 A | 8/1998 | Chambers et al. |
| 5,803,510 A | 9/1998 | Dorsey, III |
| 5,902,264 A | 5/1999 | Toso et al. |
| 5,947,990 A | 9/1999 | Smith |
| 6,148,857 A | 11/2000 | West et al. |
| 6,234,205 B1 | 5/2001 | D'Amelio et al. |

*Primary Examiner* — Scott Getzow
(74) *Attorney, Agent, or Firm* — Patrick Ikehara

(57) ABSTRACT

An electrosurgical probe for suction and irrigation systems is provided. The electrosurgical probe comprises an elongate tube with a probe tip and a probe handle. An unobstructed fluid communication path is defined by the probe handle and elongate tube.

24 Claims, 15 Drawing Sheets

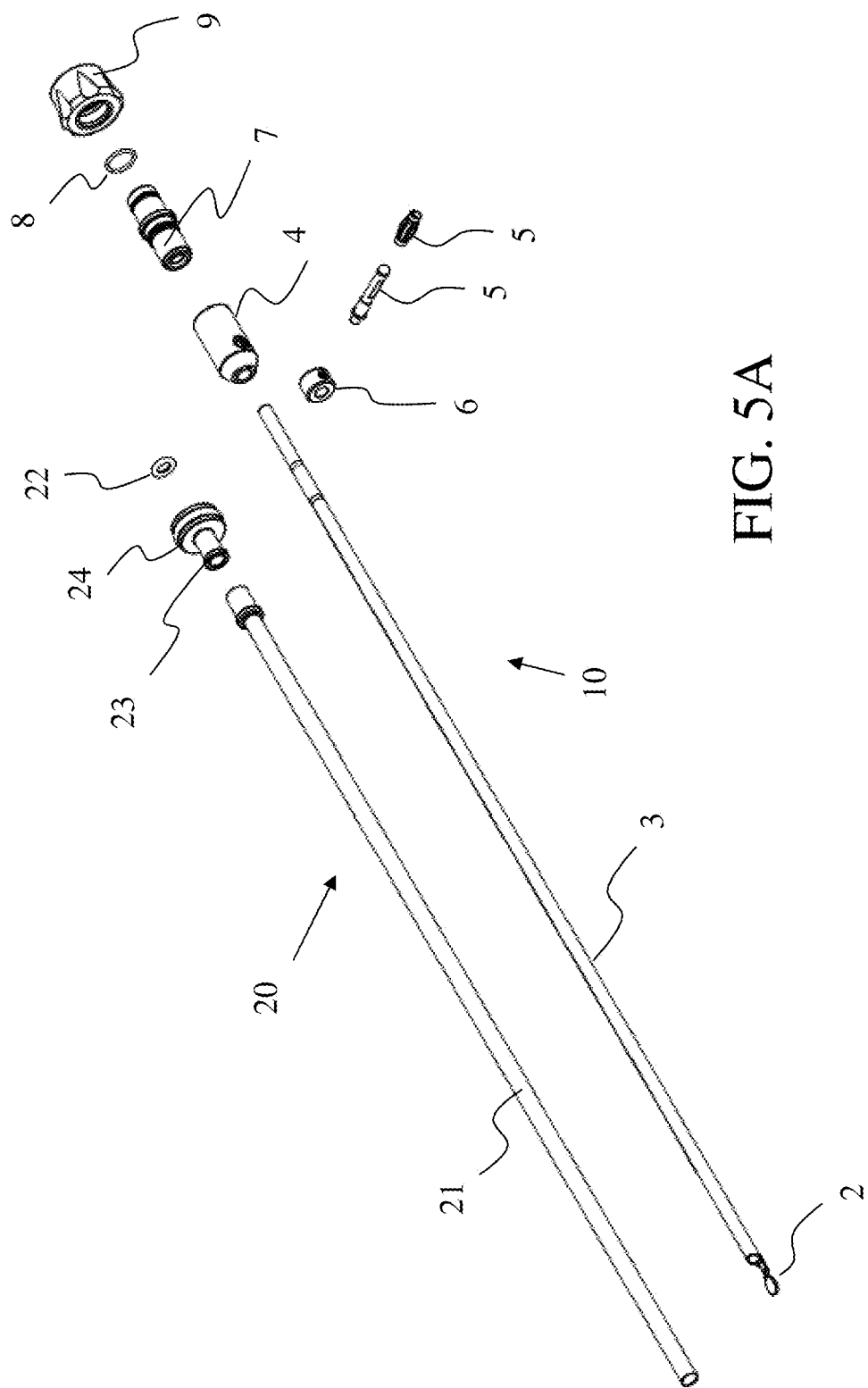

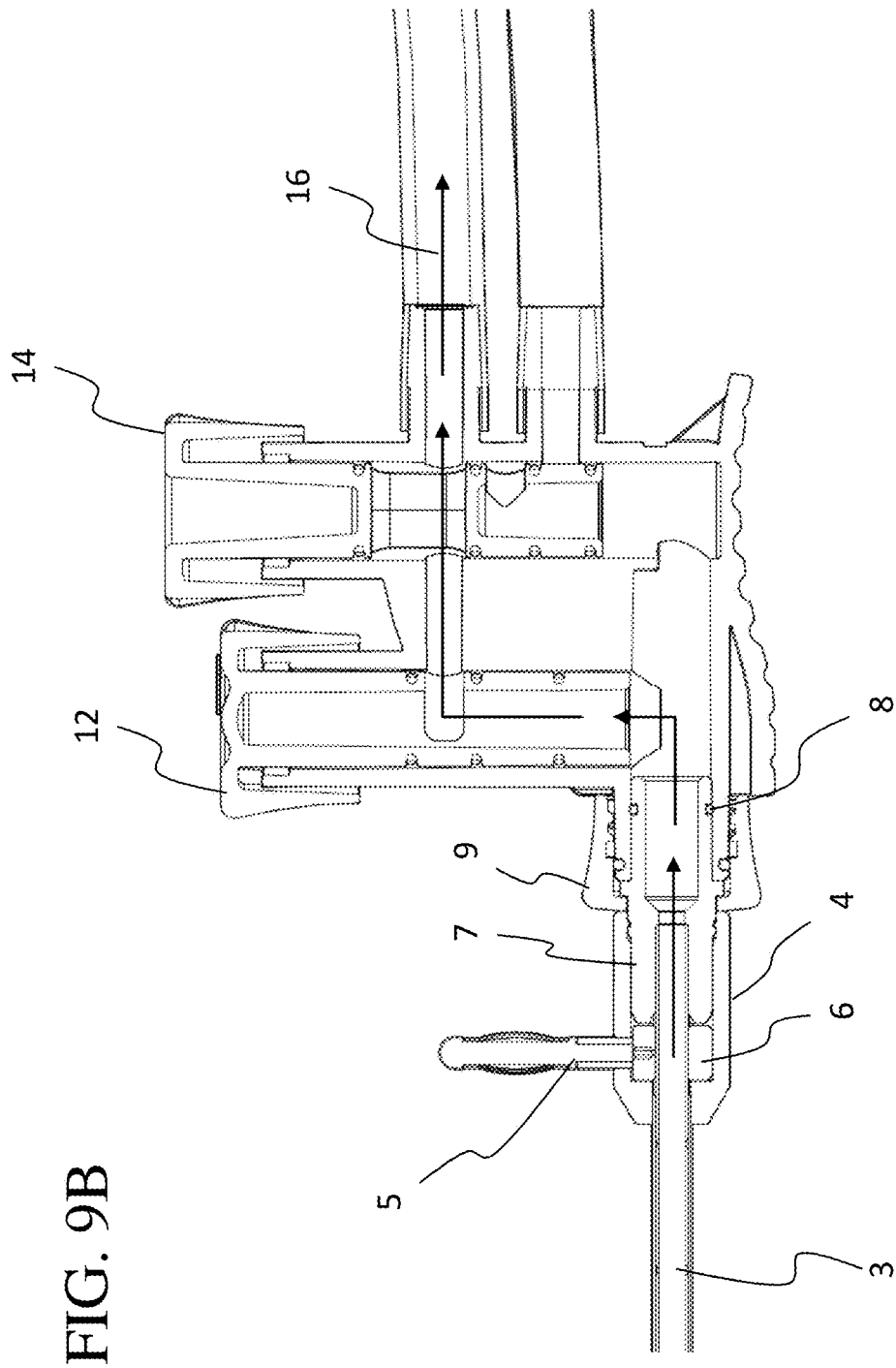

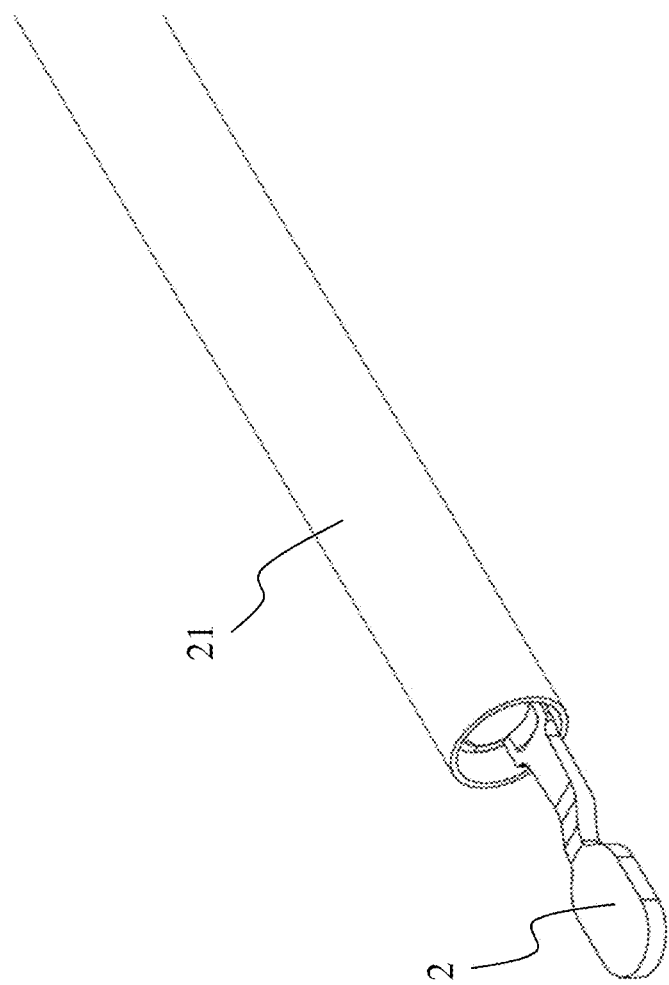

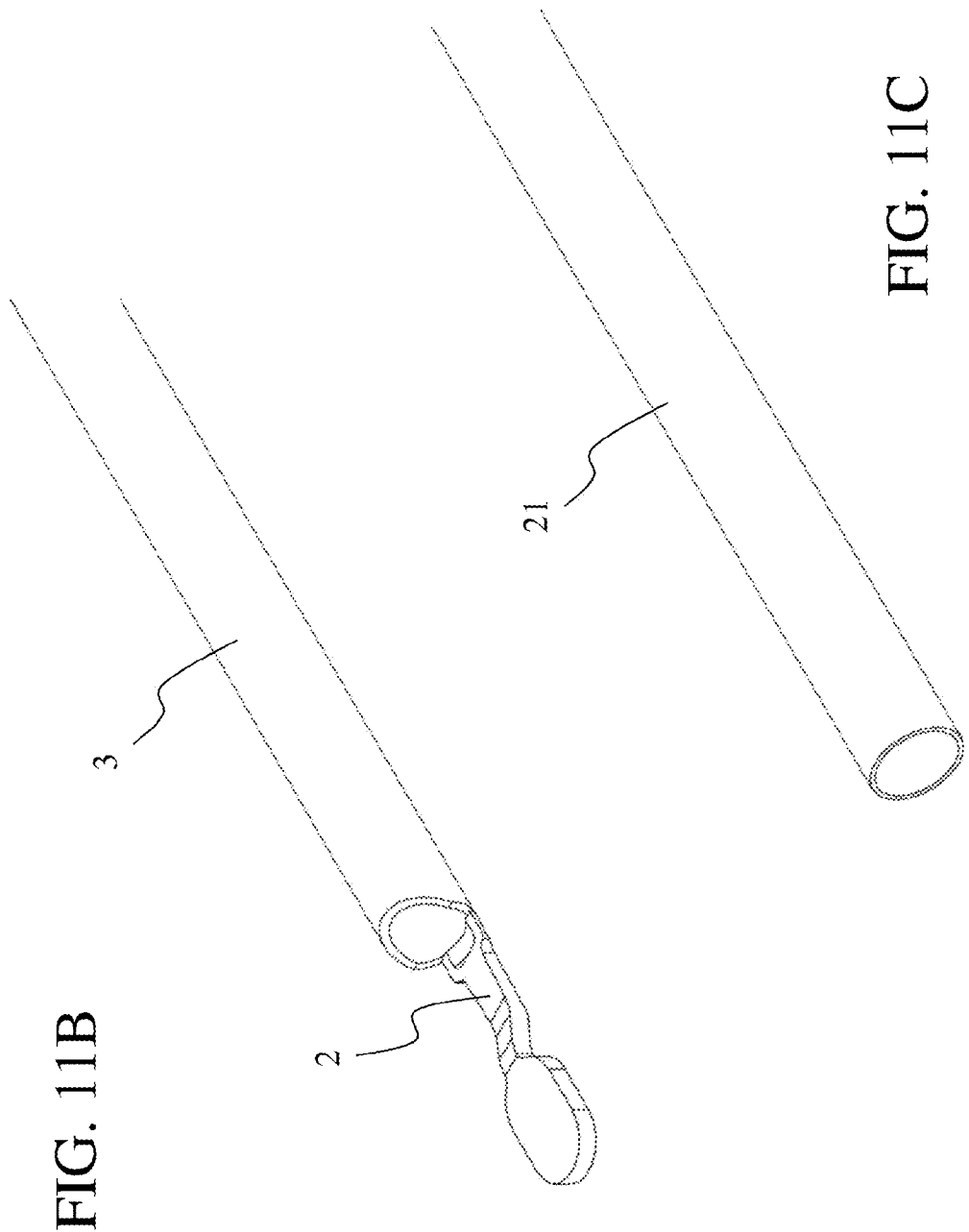

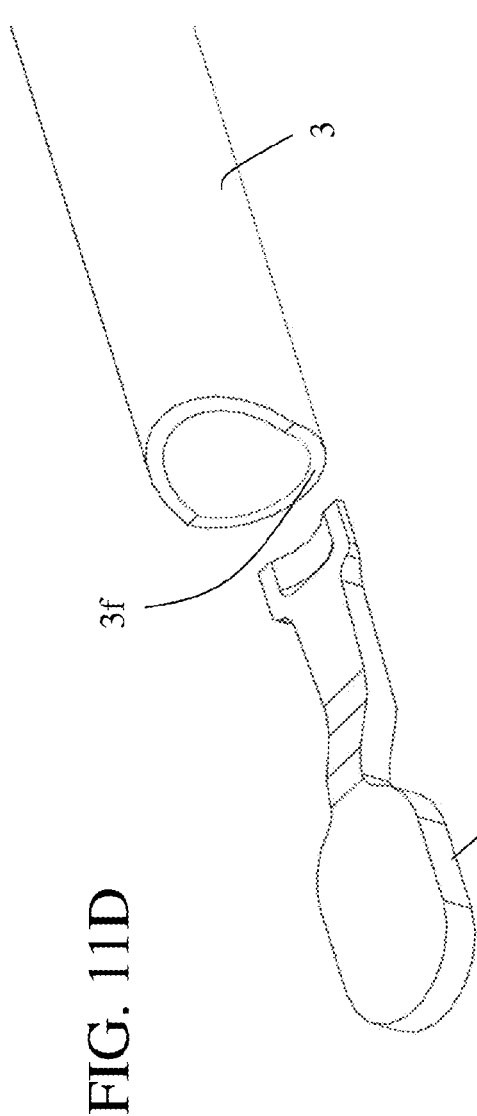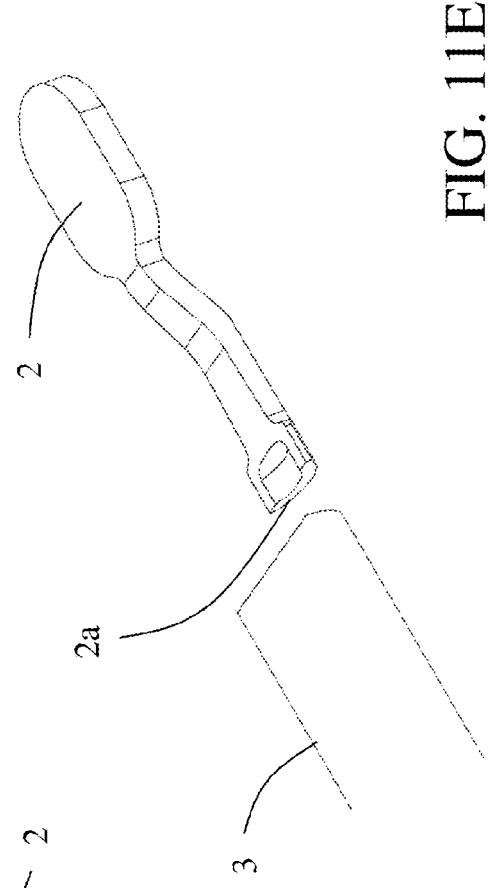

ELECTROSURGICAL PROBES FOR SUCTION AND IRRIGATION SYSTEMS

CROSS-REFERENCE TO RELATED APPLICATIONS

This application claims the benefit of U.S. Provisional Application No. 61/885,562, filed Oct. 2, 2013, the entire disclosure of which is hereby incorporated by reference as if set forth in full herein.

BACKGROUND

The present invention relates to suction and/or irrigation devices designed to deliver irrigation fluids to a surgical site and to evacuate blood, tissue debris, and smoke from the surgical site and more particularly, surgical probes arranged to be attached to suction and/or irrigation devices for use in laparoscopic surgery.

Various electrosurgical probes can be provided with various suction irrigation hand piece. Various electrosurgical probes and/or hand pieces often include complex components and the arrangement thereof that reduce or hinder the assembly or manufacturability of the probes and/or hand pieces. Furthermore, such probes and/or hand pieces provide areas or regions within such devices to trap harmful bacteria, tissue or other bodily byproducts, agents or contaminants that effect the overall operation of such devices and/or the reusability of such devices. Reusability of such devices often reduces the overall or lifetime cost of such devices. However, if poorly assembled or manufactured probes and/or hand pieces due to complex components or arrangement of such components can reduce the reusability of such devices either via the complexity of repair, the inability to appropriately sterilize such devices or increased likelihood of damage or inoperability of such device due to trapped contaminants.

SUMMARY

In accordance with various embodiments, electrosurgical probes are provided. The electrosurgical probes are slidably connectable to probe sheaths and threadably connectable to hand pieces that are connectable to suction and/or irrigation sources. In various embodiments, an electrosurgical probe comprises an elongate tube, a probe tip and a probe handle. The elongate tube has a proximal end, a distal end and an lumen extending between the proximal end to the distal end of the elongate tube and the probe tip is disposed on the distal end of the elongate tube. The probe handle has a proximal end and a distal end and is disposed on the proximal end of the elongate tube. The probe handle has a lumen extending from the proximal end of the probe handle to the distal end of the probe handle. The lumen of the probe handle is in unobstructed fluid communication with the lumen of the elongate tube and has a diameter larger than a diameter of the lumen of the elongate tube and a diameter equal to the diameter of the lumen of the elongate tube.

In accordance with various embodiments, an electrosurgical probe comprises an elongate tube, a probe tip and a probe handle. The elongate tube has a proximal end, a distal end and a lumen extending between the proximal end to the distal end of the elongate tube. The probe tip is disposed on the distal end of the elongate tube and the probe handle is disposed on the proximal end of the elongate tube. The probe handle has a probe stem with a lumen extending from a distal end of the probe stem to a proximal end of the probe stem and the proximal end of the elongate tube extends through a portion of the lumen at the distal end of the probe stem.

Many of the attendant features of the present invention will be more readily appreciated as the same becomes better understood by reference to the foregoing and following description and considered in connection with the accompanying drawings in which like reference symbols designate like parts throughout

BRIEF DESCRIPTION OF THE DRAWINGS

FIGS. 5A-B are exploded views of an electrosurgical probe and probe sheath in accordance with various embodiments of the present invention.

FIGS. 9A-C are cross-sectional side views of an electrosurgical probe and hand-piece in accordance with various embodiments of the present invention.

FIGS. 11A-E are perspective views of portions of an electrosurgical probe or probe sheath in accordance with various embodiments of the present invention.

DETAILED DESCRIPTION

An electrosurgical probe is provided for use with a suction irrigation hand piece. The electrosurgical probe includes a lumen through which fluid can be aspirated or irrigated. At the distal end of the probe a tip is provided that further enhances the operability of the probe for particular surgical procedures. The electrosurgical probe includes a probe base at the proximal end that is removably connectable to the suction irrigation hand piece. The probe base provides a lumen or unobstructed pathway from the distal end of the probe to the proximal end of the probe to the hand piece for fluid aspiration or irrigation. The electrosurgical probe is rotatable relative to the longitudinal axis of the probe and lumen therethrough. The probe base permits the probe to rotate while remaining connected to the hand piece. A probe sheath can also be included that is slidably connected to the probe. The number of components and the specific arrangement of such components for the electrosurgical probe increases and eases assembly, manufacturability and reusability of the probe.

Figure 1:
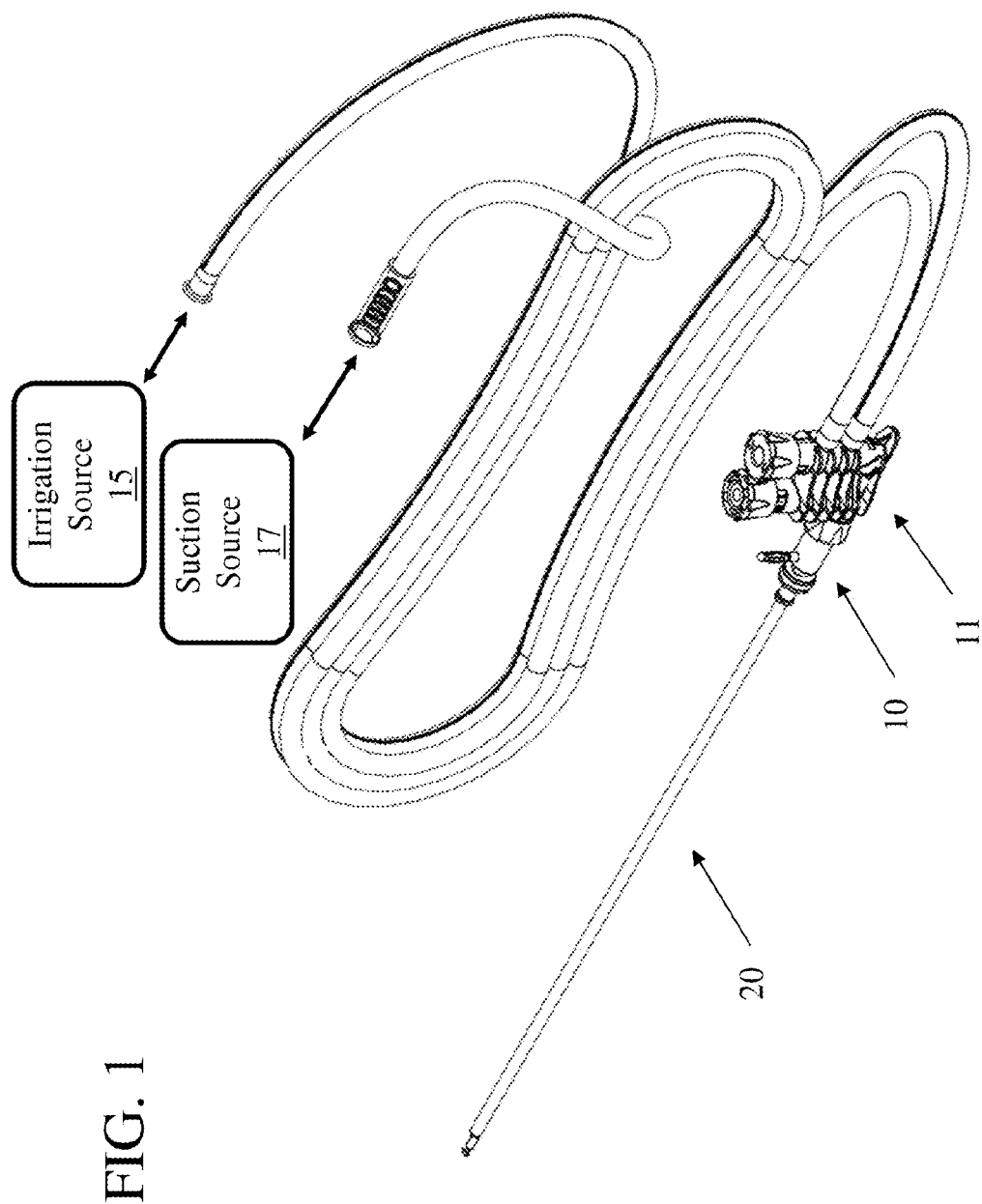
FIG. 1 is a perspective view of an electrosurgical probe and hand piece in accordance with various embodiments of the present invention.

In FIG. 1, a hand piece 11 is shown. The hand piece includes a trumpet style valve set where the activation or depression of one piston or valve 12 provides irrigation and the activation of the other valve 14 provides suction. In accordance with various embodiments, conduits are formed within the hand piece. These conduits connect an inlet on the hand piece 11 to the irrigation and/or suction valves to a common opening or outlet/inlet of the hand piece 11. The inlet of the hand piece is connected to irrigation tubing and/or other valves to receive irrigation fluid from an irrigation source 15. Likewise, the same or similar conduits or passageways are provided to connect an outlet of the hand piece to the irrigation and/or suction valves to the common opening outlet/inlet of the hand piece. The outlet of the hand piece is connected to suction tubing and/or valves for the suction or removal of fluids or gases through the application of a suction or aspiration source or pump 17 connected thereto. The common opening outlet/inlet of the hand piece is arranged to be removably connected to an electrosurgical probe.

Figure 2:
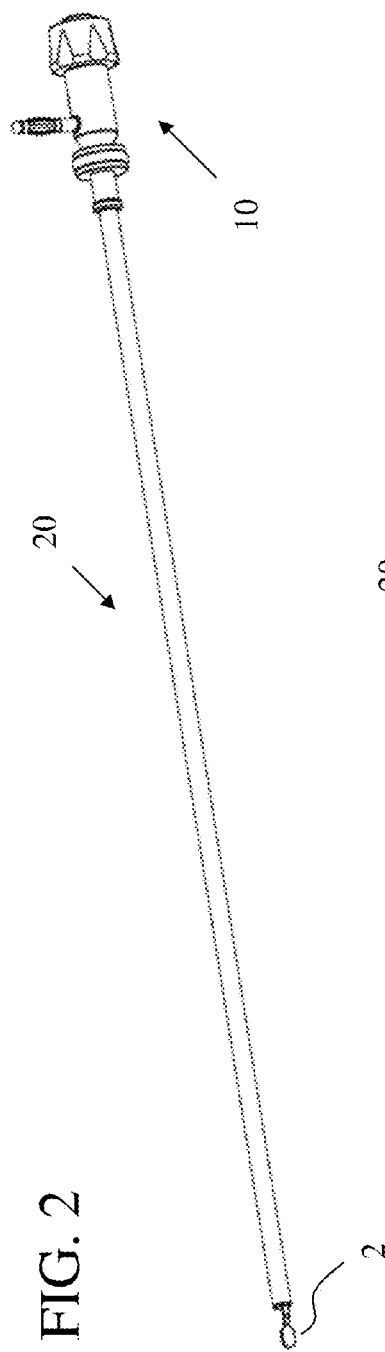
FIG. 2 is a perspective view of an electrosurgical probe and probe sheath in accordance with various embodiments of the present invention.
Figure 3:
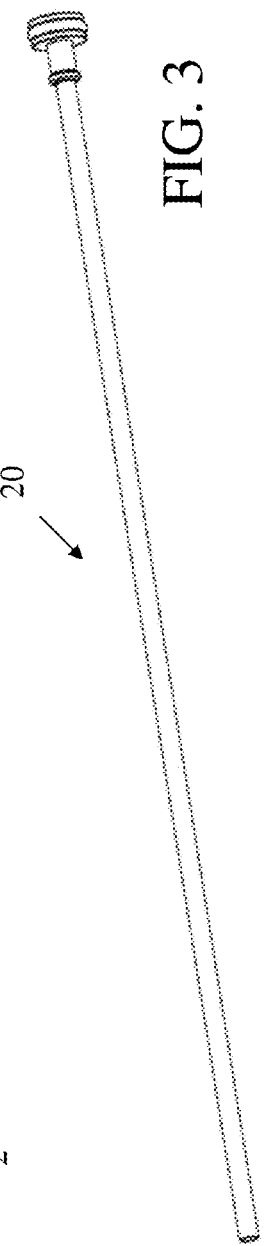
FIG. 3 is a perspective view of a probe sheath in accordance with various embodiments of the present invention.
Figure 4:
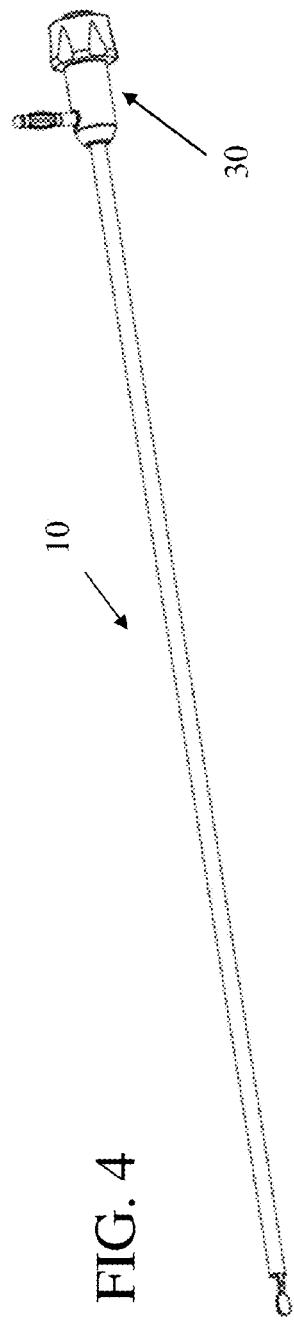
FIG. 4 is a perspective view of an electrosurgical probe in accordance with various embodiments of the present invention.

In FIG. 2, an electrosurgical probe 10 and a slidably connected probe sheath 20 are illustrated. FIG. 3 and FIG. 4 respectively show the probe sheath 20 without the probe 10 and the probe 10 without the sheath 20. The sheath 20 can slid distally to cover portions of a distal end or the tip 2 of the probe 10 to adjust flow of fluid into and/or out of the probe. Likewise, by adjusting the sheath 20, the exposure or covering of the probe tip 2 can also be accomplished.

The probe 10 and the sheath 20 are also rotatable and thus the probe and sheath can be rotated simultaneously or in unison as desired by a surgeon. The probe and sheath can also be independently rotatable. Additionally, the sheath 20 and probe 10 can be rotatable simultaneously or independently of the hand piece. As such, the sheath and/or probe can be rotated while the hand piece remains stationary and thus tubing or other connections to the irrigation and suction sources remain undisturbed and untangled.

Figure 5B:
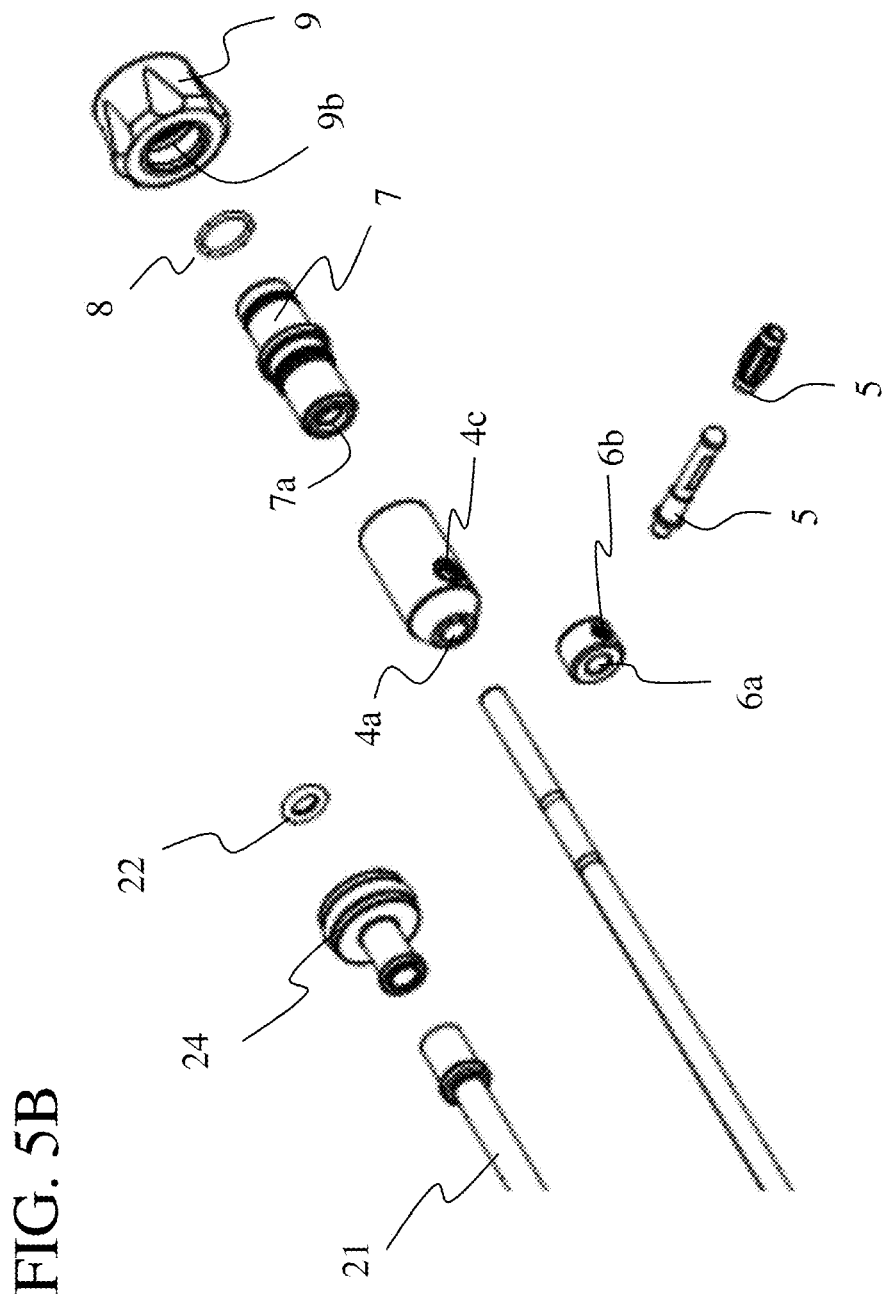
Figure 6:
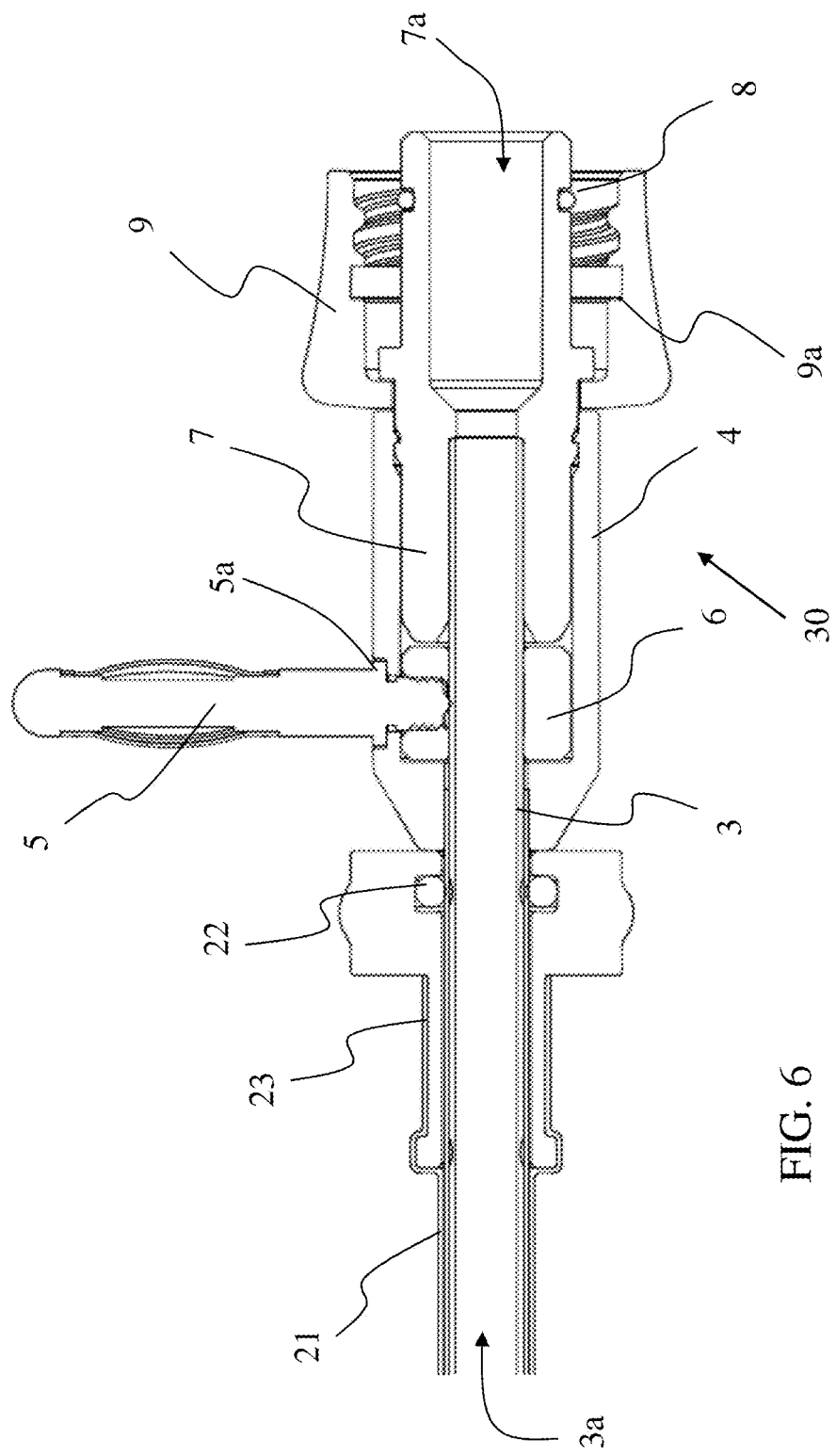
FIG. 6 is a cross-sectional side view of an electrosurgical probe and probe sheath in accordance with various embodiments of the present invention.
Figure 7:
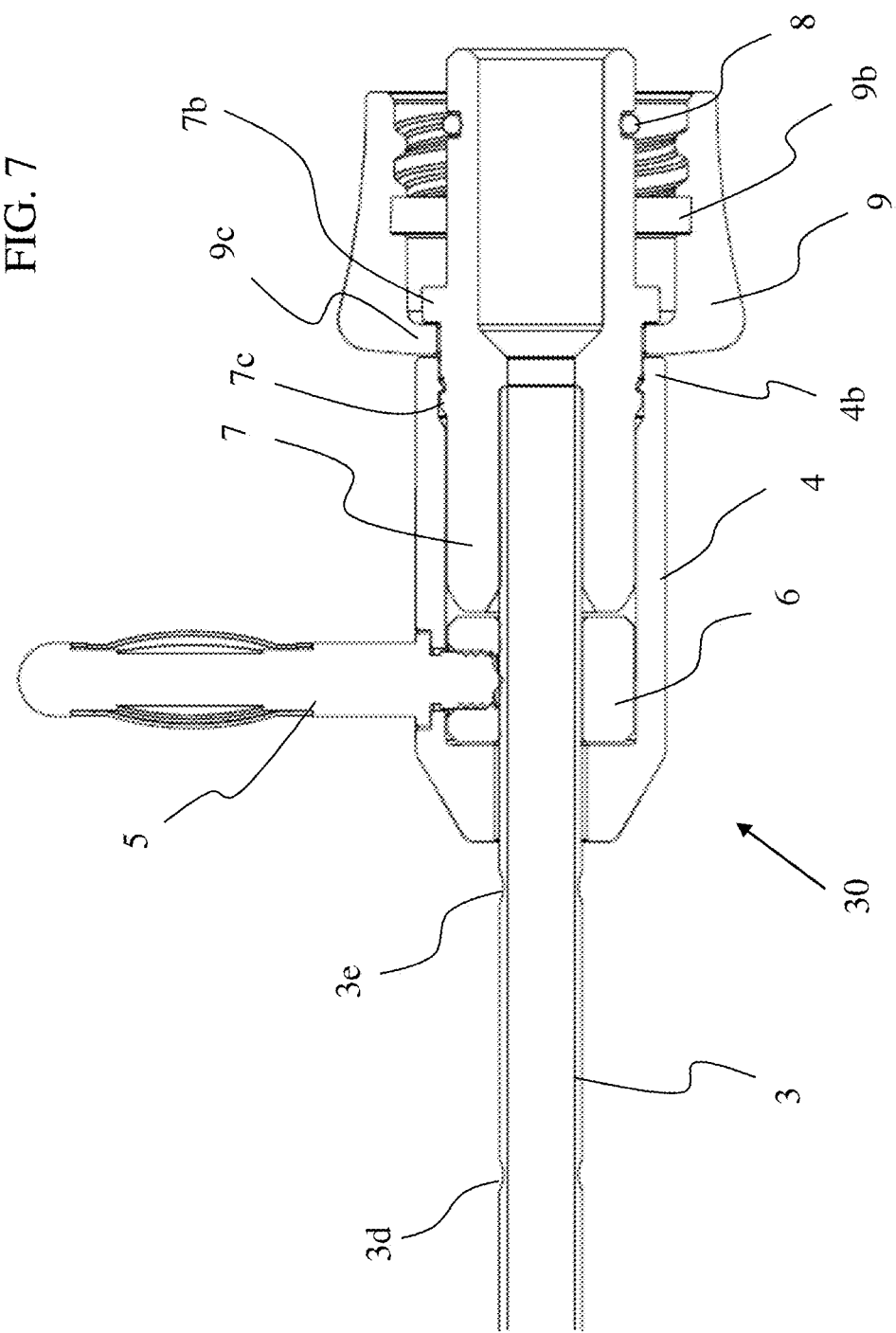
FIG. 7 is a cross-sectional side view of an electrosurgical probe in accordance with various embodiments of the present invention.

As shown in FIGS. 5-6, the probe includes a probe handle 30 with a knob 9 connected to a probe or elongate tube 3. At the distal end of the probe tube is a probe tip 2. The probe tip 2 as illustrated has a spatula configuration. The tip may have other shapes or features such as a J-hook or a L-hook. Extending through the probe tube is a lumen through which fluid can enter and exit there from. Attached to the proximal end of the probe tube 3 are a probe or pin connector 6 and a probe stem 7. The pin connector 6 is shaped like a ring or a donut with a center opening 6a extending through the longitudinal center of the pin connector. The center of the pin connector is sized and dimensioned to receive the tube 3 in which the tube 3 extends through the pin connector. The pin connector has a second aperture or hole 6b extending through or from the outer portion or periphery of the connector and to the center of the connector. The second aperture 6b is sized and dimensioned to receive the probe pin 5. In one embodiment, the probe pin 5 is threadably connected to the pin connector 6 with the probe pin having threads and the second aperture 6b of the pin connector have corresponding mating threads to releasably secure the pin to the connector. In one embodiment, the pin and pin connector are provided as a single monolithic structure. The pin and/or the pin connector directly contacts the probe tube 3 extending through the center 6a of the pin connector. The probe pin 5 is electrically coupled to a source of electrosurgical energy (not shown) based on the given surgical procedure. The probe pin 5 is conductive, e.g., made of a conductive material such as stainless steel, and the connector, the tube and the probe tip are also conductive. As such, the probe is arranged to deliver electrosurgical energy through the probe tip 2 to the surgical site. In one embodiment, a portion of the tube 3 is coated or covered with a non-conductive or insulative material extending from a distal end of the pin connector to the probe tip to ensure that electrosurgical energy is delivered at the probe tip 2 instead of along other portions of the tube. In one embodiment, the sheath provides the insulation or an additional insulation for the probe tube 3.

Referring now also to FIGS. 6-10, the proximal portion of the tube 3 extends through the center 6a of the pin connector 6 and further extends into a probe stem 7. In one embodiment, the distal end of the probe stem 7 is slighted tapered or rounded off or chamfered and the proximal and/or distal ends of the pin connector 6 are tapered or rounded off or chamfered to ease assembly of the probe 10. The probe stem 7 has a lumen 7a extending through the longitudinal center of the stem. The lumen in the distal portion is generally cylindrical and extends or flares out to a proximal cylindrical portion having a diameter greater than the distal portion of the lumen 7a. As such, the opening at the distal end or distal most end of the stem has a diameter smaller than the diameter of the opening at the proximal end or proximal most end of the stem. In one embodiment, the outer portion of the tube 3 has an outer diameter larger than the diameter of the distal portion of the lumen of the probe stem 7. As such the tube in one embodiment is press-fitted into the lumen of the probe stem and thereby securing the stem to the tube and creating a fluid tight arrangement between the tube and the stem. The inner diameter of the tube 3 equals or is substantially equal to the diameter of the distal portion of the lumen of the probe stem 7. In one embodiment, the distal portion of the lumen has a flared distal end having a diameter larger than the outer diameter of the tube and tapers proximally to a diameter smaller than the outer diameter of the tube. The flared or tapered distal end of the stem eases the connection or press-fitting of the tube into the distal portion of the lumen of the stem 7. In one embodiment, an o-ring may be disposed in a recess within the distal end of the stem to further enhance the fluid seal between the probe tube 3 and the stem 7.

The stem 7 is connected to a probe knob 9 that is threadably connected to the hand piece. As such, a probe can be threaded onto a hand piece and during the surgical procedure threaded off and another probe threaded on as desired. In one embodiment, the probe knob 9 includes a thread relief or recess 9a to prevent over threading of the probe onto the outlet of the hand piece. The probe stem 7 extends through a center opening 9b in the probe knob 9 and the stem 7 includes a projection or flange 7b that engages a projection or flange 9c of the knob 9 thereby preventing further distal longitudinal movement of the stem 7. A probe base cover 4 encases and secures the proximal portion of the stem 7 and the probe or pin connector 6 within the cover 4. A proximal end 4b of the cover 4 abuts the distal end of the knob and/or a distal outer surface of the knob or flange 9c of the knob 9. As such, this abutment and connection prevents proximal longitudinal movement of the stem 7 and thus the stem 7 is secured against longitudinal movement by the interaction of the knob, cover and flange 7b of the stem 7. However, the connection does not restrict rotational movement of the stem 7, pin connector 6, probe tube 3 and tip 2 relative to the probe knob 9. Accordingly, the probe tube 3 and tip 2 can be rotated to position the tip and tube at a particular surgical site or location while the threaded connection of the knob 9 to the hand piece remains stationary and secured. As such, the probe tube and tip can be rotated independently of the knob 9 and vice versa. Thus, inadvertent or unintended disconnection between the probe 10 and the hand piece 3 due to intended or desired rotational movement of the probe is prevented. In one embodiment, the probe 10 once attached to (e.g., thread-on) the hand-piece, the probe 10 cannot be unattached by longitudinal movement (proximally or distally) of the probe 10 and/or hand-piece 3 relative to each other.

In one embodiment, the distal portion of the stem may include ribs to ease assembly and connection of the stem within the cover 4. In various embodiments, the distal portion of the stem includes a projection, detent or slot 7c arranged to mate with a corresponding slot or detent in the cover 4 to further secure the stem 7 to the cover 4 and further restrict longitudinal movement of the stem and the probe tube 3 connected thereto.

In one embodiment, the cover 4 includes a hole or aperture 4c arranged to accommodate a distal portion of the probe pin 5 to be inserted there through and into contact with the pin connector 6. The distal portion of the probe pin 5 in one embodiment includes a flange 5a arranged to fit within a recess in the cover 4 to further secure the pin to the cover and thus to the connector 6.

The proximal portion of the stem 7 is arranged to be inserted into an outlet of the hand piece. As such, the outlet of the hand piece surrounds or encompasses the outer surface of the stem as the probe is threaded onto the outlet of the hand piece. With the connection of the hand piece to the probe a fluid path is created between the surgical site and the sources of irrigation and suction. In particular, fluid enters the proximal end of the stem 7 through the lumen 7a in the stem and directly into the lumen 3a of the probe tube 3 and out the distal end of the tube at the probe tip 2, e.g., as represented by arrows 15. Likewise, fluid can follow the reverse path, e.g., as represented by arrows 16, via suction entering the distal end of the tube at the probe tip, through the lumen 3a of the probe tube 3 and directly into the lumen 7a of the stem and into the outlet of the hand piece. In one embodiment, an o-ring 8 is provided on the outer surface of the stem 7 to ensure a fluid tight connection between the hand piece outlet and the stem. The o-ring 8 in one embodiment is disposed on the inner surface of the stem 7 in various embodiments in which the outlet of the hand piece is inserted into the stem 7 instead of the stem 7 being inserted and encompassed by the outlet of the hand piece.

As shown and described above, the fluid path between the outlet and the distal end of the probe tube 3 is fully contained and isolated to the lumens of the tube 3a and the stem 7a. With such an isolated fluid path, e.g., as represented by arrows 15, 16, potential leaks along the entire fluid path, i.e., from the distal end of the probe 10 at the surgical site to the proximal end of the probe 10 connected to the hand piece, are prevented or minimized. Preventing or minimizing leaks/contaminants from the patient enhances reusability of the probe as sterilization of the probe is eased. In other words, spaces or openings within the probe (e.g., within cover 4 or knob 9 or between these components and/or the stem 7 and connector 6) are minimized to prevent contaminants from being trapped within the probe. Such trapped contaminants may prevent the probe from being reused as the inability to remove such agents or byproducts via sterilization or the continual build up of such contaminants becomes unacceptable (e.g., the probe cannot be successfully autoclaved at least 25 times). Creating a contained and isolated fluid path prevents such contaminants from entering or being trapped within the probe in the first place and therefore enhances reusability or the successful or acceptable sterilization of the probe. In one embodiment, the probe stem 7 and the probe tube 3 are formed as a single monolithic piece or structure further containing and isolating the fluid path and thereby minimizing potential leaks along the entire fluid path of the probe. As such, in accordance with various embodiments, the isolated fluid flow or path consists only of or through the lumen in the stem 7 and directly into the lumen of the probe tube 3 and vice versa, e.g., no intermediary components.

Figure 10:
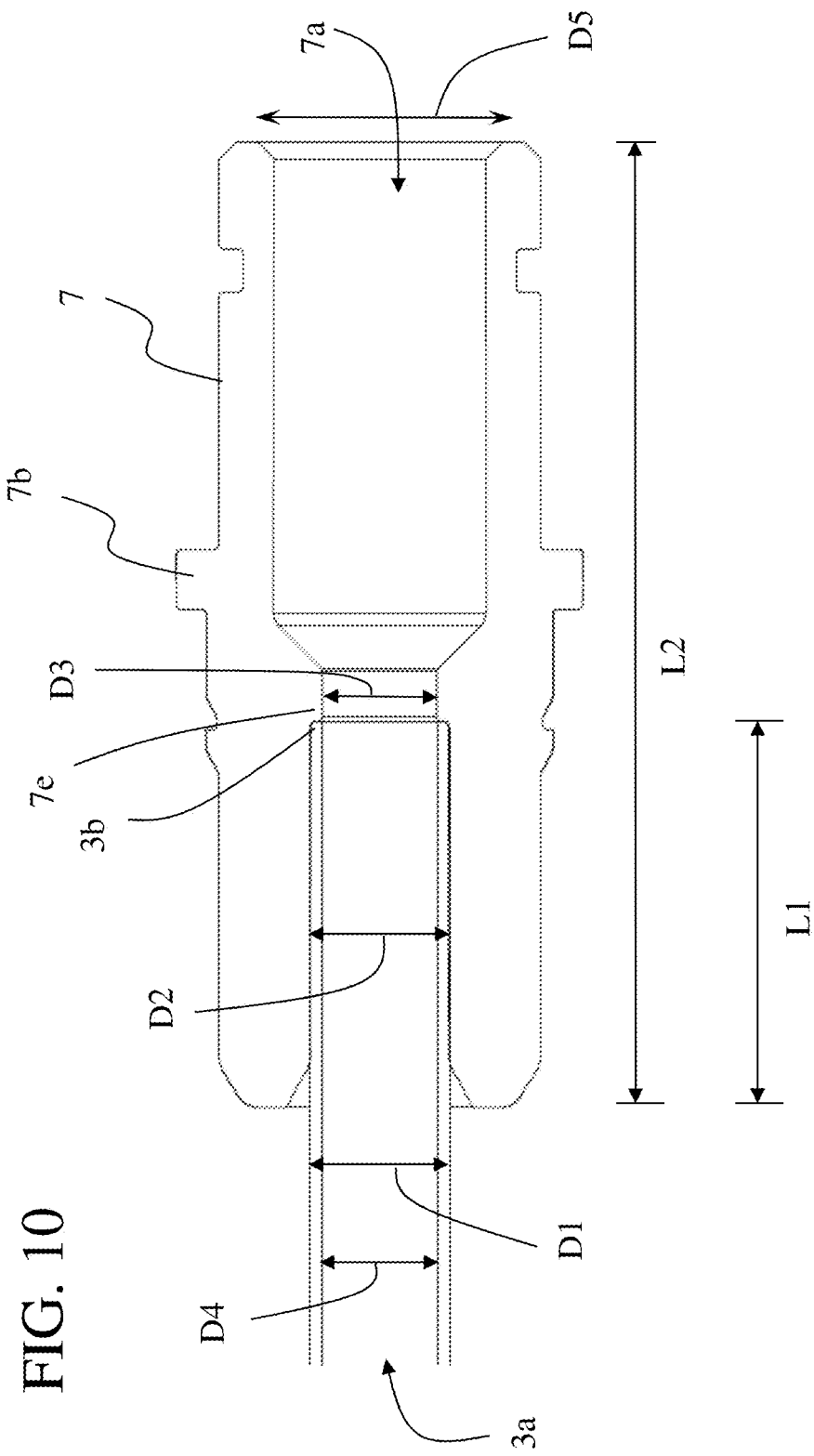
FIG. 10 is a cross-sectional side view of a portion of an electrosurgical probe in accordance with various embodiments of the present invention.

Further details regarding the isolated fluid path can be seen in FIG. 10 in which an enlarged view of the probe stem and probe tube with other components removed are shown. The outer diameter D1 of the probe tube is larger than the inner diameter D2 of the probe stem. Extending proximally, the distal portion of the lumen of the probe stem has a diminishing inner diameter and the proximal portion of the lumen of the probe stem has an increasing inner diameter with the largest inner diameter D5 being at the most proximal end of the lumen. The inner diameter at the proximal most end of the lumen is larger than the distal most end of the lumen of the probe stem. The tube is slid into the distal portion of the lumen in a press-fit manner in which the proximal portion of the probe tube 3 is compressed against the inner surface of the lumen of the probe stem 7. A flat proximal wall 3b of the probe tube which is perpendicular to the longitudinal lumen 3a of the tube also pressed against a corresponding flat wall 7e of the stem 7 thereby abutting the walls together. At this point or area, the inner diameter D3 of the lumen is smaller than the outer diameter D1 of the probe tube but equal to or smaller than the inner diameter D4 of the probe tube further ensuring a direct fluid path and minimizing potential leak paths. The inner diameter D3 of the lumen 7a remains constant for a particular length before increasing in size to be a size larger than the outer diameter D1 of the probe tube. The increased size enhances the ingress/egress of fluid into and out of the probe and into/out of the outlet of the hand piece. The proximal most diameter D5 of the lumen being equal to or substantially equal to the inner diameter of the outlet of the hand piece further enhances the flow path. Additionally, the increased diameter sizes relieve or diffuse any potential pressure build up with the introduction or removal of fluid.

Furthermore, distal portion of the length L1 of the probe tube is at least third or more of the entire length L2 of the probe stem 7 and thus removes or minimizes any gap between the proximal end of the tube and the distal end of the stem and provides further structural support to prevent disengagement of the tube from the stem. Tube has a uniform inner surface that is unobstructed or uninterrupted being smooth with no apertures or detents or recesses to maximize fluid flow. The inner diameter of the proximal portion of the tube and the distal end of the stem being uniform or substantially uniform further maximizes fluid flow and further reduces potential leak paths. Periphery size and shape matches of the outer surface of the probe tube and inner surface of the lumen in various embodiments also enhance the connection and thus the fluid pathway of the probe. Additionally, even if leaks between the tube and stem occur, nooks, crevices or spaces in which contaminants may get trapped in the probe are minimized or eliminated.

Figure 8:
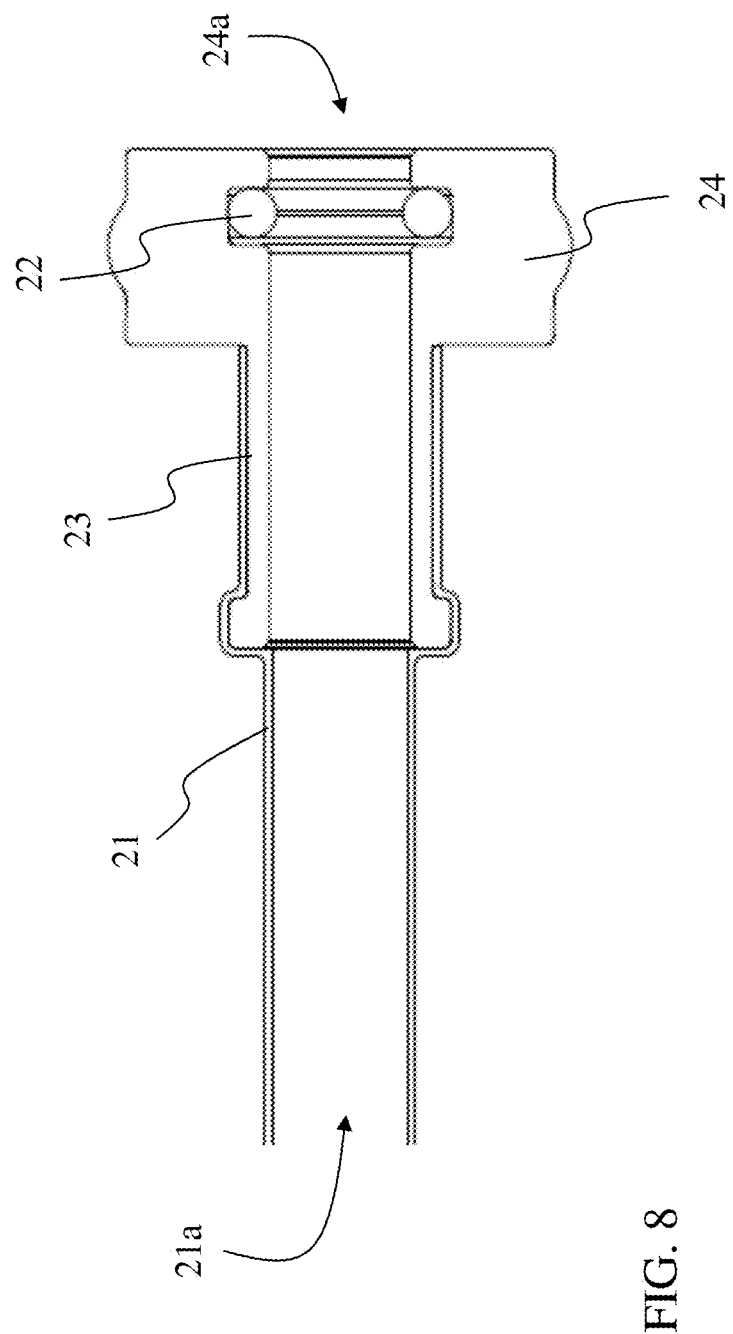
FIG. 8 is a cross-sectional side view of a probe sheath in accordance with various embodiments of the present invention.
Figure 9A:
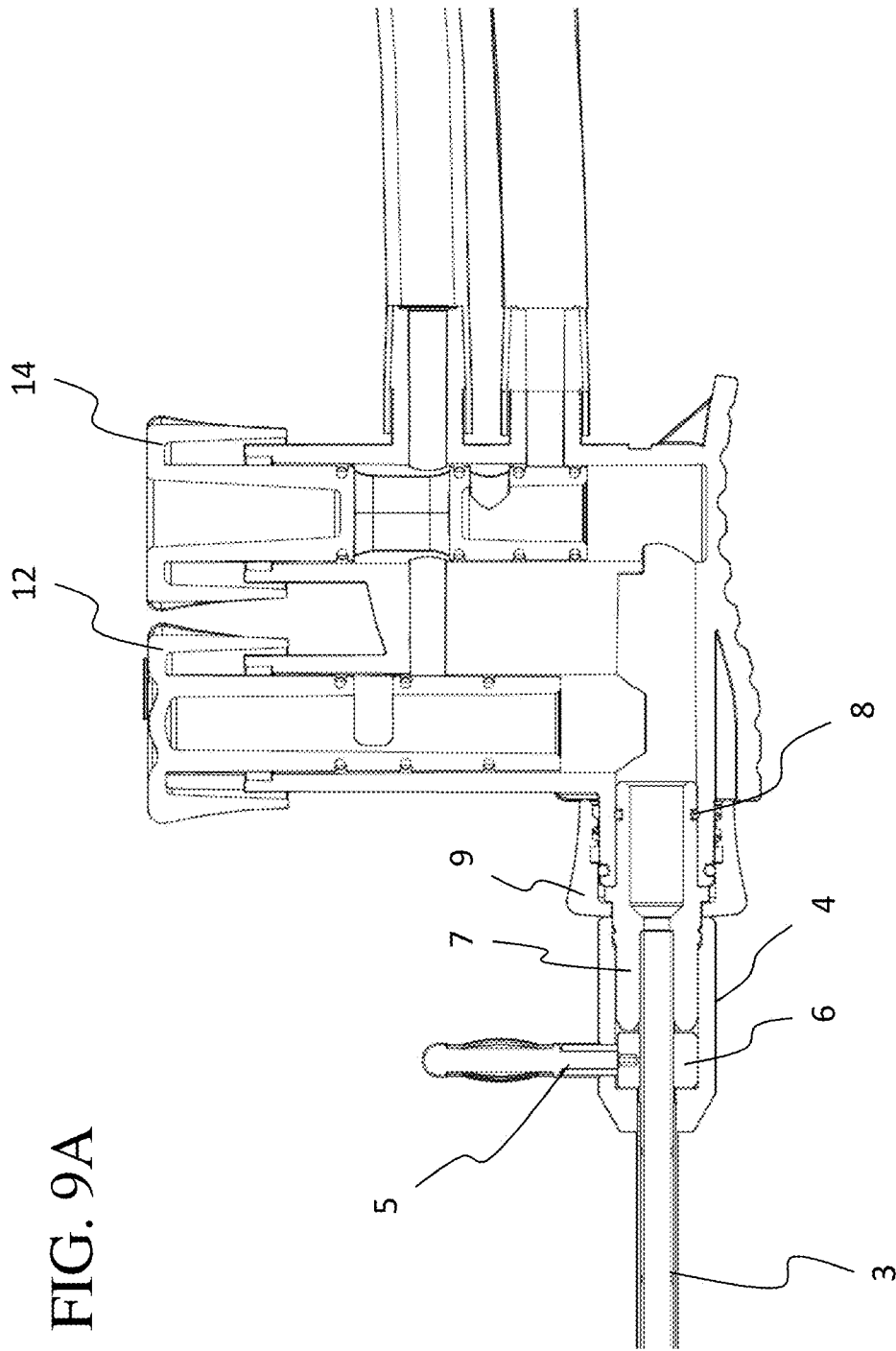
Figure 9C:
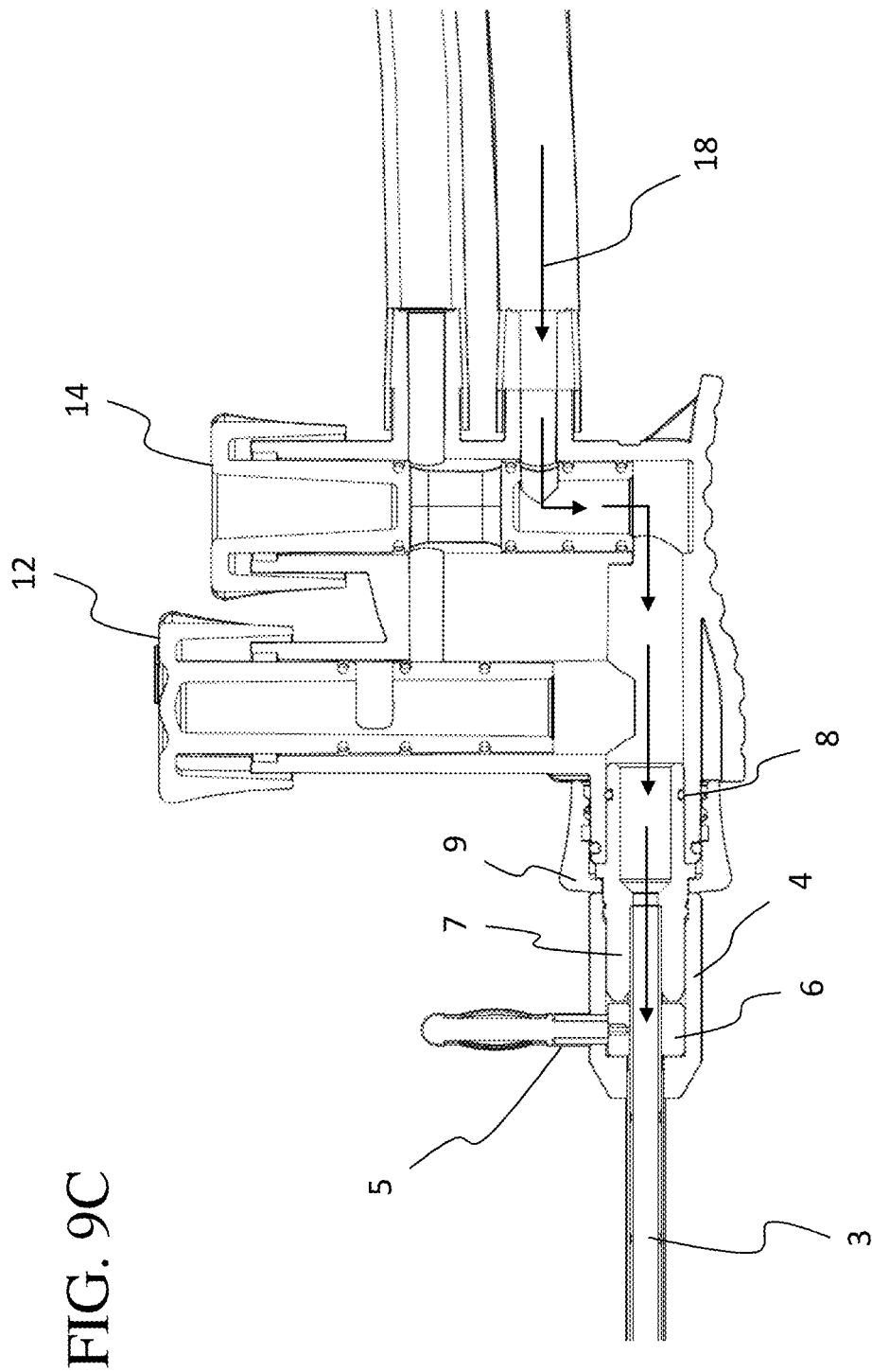

As shown in FIGS. 6 and 8, the probe sheath 20 includes a sheath tube 21 with a lumen 21a extending from a distal end and a proximal end of the sheath. The distal end in various embodiments includes an aperture or hole in the side wall or outer wall of the sheath tube to vary fluid flow or exposure of the probe tip as desired. The proximal end of the sheath tube 21 includes an enlarged portion in which a proximal portion 23 of the sheath handle 24 is inserted therein. In one embodiment, the proximal end of the sheath tube 21 is shrink-fitted over the proximal portion 23 of the sheath handle. The sheath handle has a lumen 24a with a diameter equal or substantially equal to the diameter of the lumen 21a in the sheath tube. At the proximal end of the sheath handle 24 is a recess arranged to hold a sheath o-ring 22 therein to prevent leaking or exiting/entry of fluid between the sheath 20 and the probe 10 when both are releasably connected to each other. The o-ring 22 is engagable with slots or divots 3d, 3e in the outer surface of the probe tube 3 to further enhance the sealing relationship between the probe tube 3 and the sheath handle 24. These one or more engagement points o-ring 22 with slots 3d or slot 3e further provide tactile feedback to the surgeon of the relationship of sheath tube 21 relative to the probe tube 3 and the probe tip 2. For example, the sheath base engaging a first recess 3d indicates that the probe tip is covered by the distal end of the probe sheath tube 21 and the sheath base engaging a second recess 3e indicates that the probe tip is uncovered or fully exposed.

The sheath 20 also includes a sheath knob at the proximal end of the sheath tube 21 attached to or integral with the sheath handle 24. The sheath knob in the illustrated embodiment is enlarged or has an outer diameter larger than the outer diameter of the sheath tube and arranged to be manipulated by a surgeon to move the sheath in a sliding fashion or longitudinal direction relative to the probe 10 and/or rotate the sheath relative to the probe 10.

FIGS. 11A-E illustrate a distal end of the probe sheath 20 and the probe 10 in which the probe tip 2 extends from the probe tube 3. The probe tip 2 in the illustrated embodiment is a spatula tip. The probe tip 2 has a proximal base end that is welded directly to the distal end of the probe tube 3. In particular, an outer distally facing flat wall 3f of the probe tube 3 is disposed along a plane perpendicular to the longitudinal axis or lumen 3a of the probe tube 3. Similarly, an outer proximally facing flat wall 2a of the proximal base end of the probe tip 2 is disposed along a plane perpendicular to the longitudinal axis or lumen 3a of the probe tube 3. Both flat walls 3f and 2a abut each other and are welded together. As such, the lumen and the inner and outer surfaces of the probe tube remain unblemished or undisturbed. Likewise, the lumen 3a of the probe tube is unobstructed by such blemishes and unobstructed at the distal end of the tube with the base of the tip being directly connected to the flat wall of the probe tube and not to the interior and exterior of probe tube.

Figure 12:
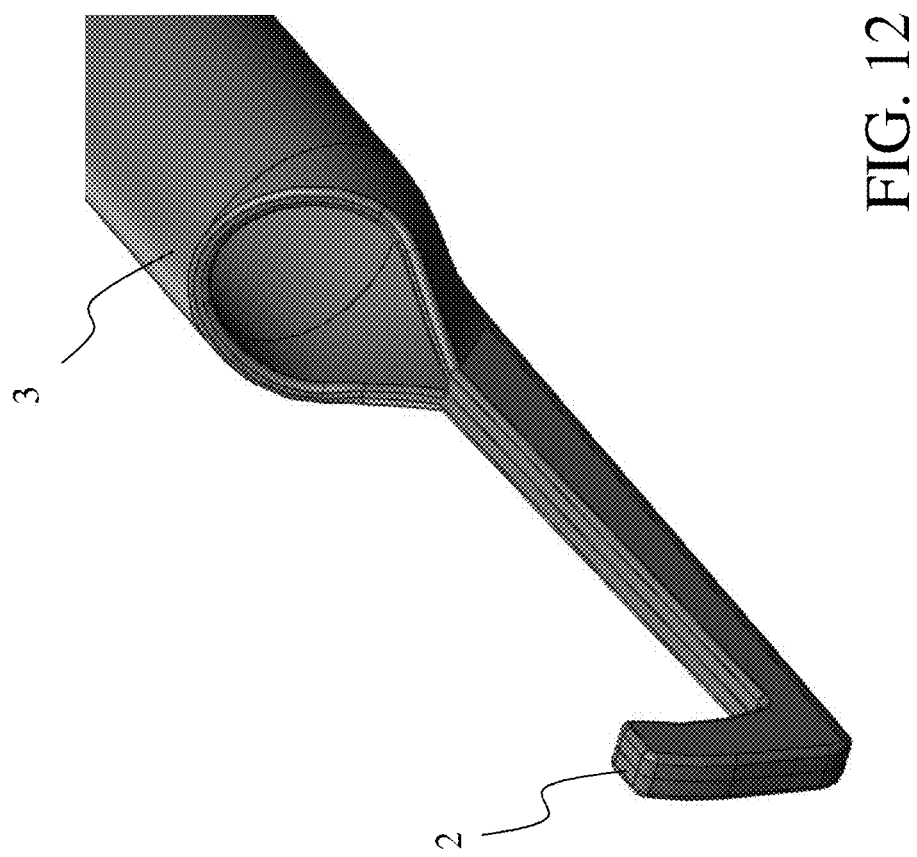
FIG. 12 is a perspective view of a portion of an electrosurgical probe in accordance with various embodiments of the present invention.

In one embodiment, as shown in FIG. 12, the distal end and the probe tip of the probe is formed by stamping the distal end to form a generally flat portion and then the desired shape, e.g., a J-hook, L-hook, spatula, etc., of the probe tip is punched or cut out. As shown, the lumen of the probe remains unobstructed with a more tear dropped opening formed at the distal end of the probe. Manufacturing of the probe is thus eased however portions or crevices can be created at the folded portions of the tip that may trap contaminants making sterilization unacceptable and thus reusability likewise unacceptable. However, forming the probe in such a manner can prove useful for disposable probes, i.e., probes not intended or provided for reuse.

In accordance with various embodiments, the tip acts as an electrode to be used in a monopolar electrosurgical system. Also, in accordance with various embodiments, the manufacturing of the electrosurgical probe and sheath are provided to ensure an isolated fluid path is created. For the probe 10 for example a probe tip 2 is welded or stamped at the distal end of a stainless steel tube, e.g., probe tube 3. A plastic tube, e.g., made of PTFE, is heat-shrunk over the tip and probe tube connection and then another plastic tube, e.g., made of FEP, is heat-shrunk over the previous tube and the remainder of the probe tube up to a proximal portion of the tube 3. The proximal portion of the tube thus being exposed. In one embodiment, a single plastic tube is utilized for the tip and tube connection and the remainder of the probe tube. The pin connector is slid over the tube up to the end of the plastic tube where the proximal portion of the tube is exposed. The stem is slid over the tube to abut the pin connector. In one embodiment, the tube is press-fitted into the lumen of the stem until the tube abuts the wall or flange of the stem. The o-ring is installed on the stem and the knob over and on top of the stem and o-ring. The cover is placed over the pin connector and the rest of the stem not covered by the knob. The openings in the cover and pin connector are aligned and the pin is threaded through the cover and the pin connector. Regarding the sheath 20, in accordance with various embodiments, an o-ring is installed in the sheath handle and a plastic tube, e.g., made of FEP, is heat-shrunk over a proximal portion of the sheath handle. In one embodiment, multiple heating steps are performed and a mandrel is used to ensure the sheath tube remains cylindrical during the heating of the tube and the handle to ensure connection between the handle and tube. The mandrel is removed after the tube is formed. One or more holes are punched at the distal end of the probe as desired.

In accordance with various embodiments, the probe handle and elongate or probe tube are permanently affixed together and/or cannot be disassembled or disconnected relative to each other and in various embodiments, the probe stem and elongate tube are permanently affixed together and/or cannot be disassembled or disconnected relative to each other. In accordance with various embodiments, the probe stem, probe base cover, probe knob, pin connector, elongate tube, probe tip and any combination thereof are permanently affixed together and/or cannot be dissembled or disconnected relative to each other.

It should be noted that fluid is used throughout for clarity sake but should not be limited to fluids such as irrigation fluids but should also include air, carbon dioxide, blood, medicines, therapeutics and other such fluids and/or gases that may be introduced into or removed from a patient for a given surgical procedure. Additionally, although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. As such, it should be appreciated that although specific combinations of embodiments and features or aspects of various embodiments may not be explicitly described such combinations however are contemplated and within the scope of the present inventions. Thus, it is intended that the scope of the present inventions herein disclosed should not be limited by the particular disclosed embodiments described above.

The invention claimed is:

1. An electrosurgical probe comprising:
   an elongate tube having a proximal end, a distal end and an lumen extending between the proximal end to the distal end of the elongate tube;
   a probe tip disposed on the distal end of the elongate tube; and
   a probe handle having a proximal end and a distal end, the distal end of the probe handle being disposed on the proximal end of the elongate tube and the probe handle having a lumen extending from the proximal end of the probe handle to the distal end of the probe handle, the lumen of the probe handle being in unobstructed fluid communication with the lumen of the elongate tube and having a diameter larger than a diameter of the lumen of the elongate tube and a diameter equal to the diameter of the lumen of the elongate tube.

2. The probe of claim 1 wherein the probe tip is formed by stamping the distal end of the elongate tube to form a flat portion and a probe tip shape is punched out from the flat portion.

3. The probe of claim 2 wherein the probe tip shape is one of a J-hook, an L-hook or a spatula.

4. The probe of claim 3 wherein the lumen of the elongate tube adjacent the probe tip has a tear dropped shape opening.

5. The probe of claim 1 wherein the probe handle comprising a pin connector having a donut shape with a center opening extending through a longitudinal center of the pin connector, the proximal end of the elongate tube extending through the longitudinal center of the pin connector.

6. The probe of claim 5 wherein the pin connector has an aperture extending through an outer periphery of the pin connector and to the longitudinal center of the pin connector and further comprising a probe pin extending through the aperture and contacting the proximal end of the elongate tube.

7. The probe of claim 6 wherein the probe pin, pin connector and elongate tube are made of the same conductive material.

8. The probe of claim 1 the probe handle has only a single o-ring seal at the proximal end of the probe handle.

9. The probe of claim 8 further comprising a hand piece coupled to an irrigation source and a suction source and having an outlet having an outer surface and an inner surface, the o-ring of the probe handle in direct contact with the inner surface of the outlet and the outer surface of the outlet being threadably connectable to a probe knob of the probe handle.

10. An electrosurgical probe comprising:
    an elongate tube having a proximal end, a distal end and an lumen extending between the proximal end to the distal end of the elongate tube;
    a probe tip disposed on the distal end of the elongate tube; and
    a probe handle being disposed on the proximal end of the elongate tube and having a probe stem, the probe stem having a lumen extending from a distal end of the probe stem to a proximal end of the probe stem, the proximal end of the elongate tube extending through a portion of the lumen at the distal end of the probe stem, the probe stem having proximal and distal taper ends.

11. The probe of claim 10 wherein the proximal end of the elongate tube is press fitted into the distal end of the lumen of the probe stem.

12. The probe of claim 10 wherein the probe stem and the elongate tube defines an isolated fluid path, the isolated fluid path consisting only of the lumen of the elongate tube directly connected to the lumen of the probe stem.

13. The probe of claim 12 further comprising an outlet of a hand piece directly connected to the isolated fluid path.

14. An electrosurgical probe comprising:
    an elongate tube having a proximal end, a distal end and an lumen extending between the proximal end to the distal end of the elongate tube;
    a probe tip disposed on the distal end of the elongate tube; and
    a probe handle being disposed on the proximal end of the elongate tube and having a probe stem, the probe stem having a lumen extending from a distal end of the probe stem to a proximal end of the probe stem, the proximal end of the elongate tube extending through a portion of the lumen at the distal end of the probe stem and the lumen of the probe stem has a cylindrical distal portion and a cylindrical proximal portion, the cylindrical proximal portion having a diameter greater than a diameter of the cylindrical distal portion.

15. The probe of claim 14 wherein the cylindrical distal portion has a diameter smaller than an outer diameter of the elongate tube.

16. The probe of claim 14 wherein the elongate tube has an inner diameter and the distal portion of the probe stem has an inner diameter, the inner diameter of the elongate tube being equal to the inner diameter of the distal portion of the probe stem.

17. An electrosurgical probe comprising
    an elongate tube having a proximal end, a distal end and an lumen extending between the proximal end to the distal end of the elongate tube;
    a probe tip disposed on the distal end of the elongate tube; and
    a probe handle being disposed on the proximal end of the elongate tube and having a probe stem, the probe stem having a lumen extending from a distal end of the probe stem to a proximal end of the probe stem, the proximal end of the elongate tube extending through a portion of the lumen at the distal end of the probe stem and the proximal end of the elongate tube has an outer diameter larger than a diameter of a distal portion of the lumen of at the distal end of the probe stem, the proximal end of the elongate tube being in direct contact with the distal portion of the lumen of the probe stem.

18. An electrosurgical probe comprising:
    an elongate tube having a proximal end, a distal end and an lumen extending between the proximal end to the distal end of the elongate tube;
    a probe tip disposed on the distal end of the elongate tube; and
    a probe handle being disposed on the proximal end of the elongate tube and having a probe stem, the probe stem having a lumen extending from a distal end of the probe stem to a proximal end of the probe stem, the proximal end of the elongate tube extending through a portion of the lumen at the distal end of the probe stem and the lumen of the probe stem has a flared distal end having a diameter larger than an outer diameter of the elongate tube and the flared distal end of the lumen tapers proximally to a diameter smaller than the outer diameter of the elongate tube.

19. The probe of claim 18 further comprising a probe knob and a hand piece, the probe stem being connected to the probe knob and the probe knob threadably connected to the hand piece.

20. The probe of claim 19 wherein the probe knob has a center opening and the probe stem extends through the center opening of the probe knob; and the probe stem has a flange near a mid-section of the probe stem that engages a flange of the probe knob, the engagement of the flange of the probe stem and the flange of the probe knob preventing distal longitudinal movement of the probe stem and simultaneously not restricting rotational movement of the probe stem relative to the probe knob.

21. The probe of claim 20 further comprising a pin connector and a probe base cover, the probe base cover encasing a proximal portion of the probe stem and the pin connector, the probe base cover including a proximal end that abuts a distal end of the probe knob, the abutment of the probe base cover and the distal end of the probe knob preventing proximal longitudinal movement of the probe stem and simultaneously not restricting rotational movement of the probe stem relative to the probe knob, and wherein the pin connector, the probe base cover, the probe stem and the elongate tube are permanently affixed together and not disconnectable from each other.

22. The probe of claim 21 wherein a proximal portion of the probe stem is insertable into an outlet of a hand piece, the outlet of the hand piece surrounding an outer surface of the probe stem, the hand piece having a first valve arranged to selectively connect the hand piece, the lumen of the probe stem and the lumen of the elongate tube to an irrigation source and having a second valve arranged to selectively connect the hand piece, the lumen of the probe stem and the lumen of the elongate tube to a suction source.

23. The probe of claim 22 wherein an o-ring is disposed between the outer surface of the probe stem and the outlet of the hand piece and the probe knob is threadably connectable to threads on an outer surface of the outlet of the hand piece.

24. An electrosurgical probe comprising:
  an elongate tube having a proximal end, a distal end and an lumen extending between the proximal end to the distal end of the elongate tube;
  a probe tip disposed on the distal end of the elongate tube; and
  a probe handle being disposed on the proximal end of the elongate tube and having a probe stem, the probe stem having a lumen extending from a distal end of the probe stem to a proximal end of the probe stem, the proximal end of the elongate tube extending through a portion of the lumen at the distal end of the probe stem and the distal end of the elongate tube has an outer distally facing flat wall disposed along a plane perpendicular to a longitudinal axis of the elongate tube and the probe tip has a proximal end with an outer proximally facing flat wall disposed along a plane perpendicular to the longitudinal axis of the elongate tube, both flat walls abutting each other and welded together.

* * * * *